United States Patent [19]

Buchmann et al.

[11] Patent Number: 4,812,407

[45] Date of Patent: Mar. 14, 1989

[54] MEMBRANE, SYSTEM AND PROCESS FOR TESTING SUBSTANCE DIFFUSION THROUGH THE MEMBRANE AND METHOD FOR MAKING THE MEMBRANE

[75] Inventors: Stephan Buchmann, Munchenstein; Hans Leuenberger, Pfeffingen, both of Switzerland; Claudia Reinke, Freiburg Im Breisgau, Fed. Rep. of Germany

[73] Assignee: Pharmatronic AG, Pratteln, Switzerland

[21] Appl. No.: 38,285

[22] Filed: Apr. 14, 1987

[30] Foreign Application Priority Data

Apr. 15, 1986 [CH] Switzerland ............ 1496/86

[51] Int. Cl.⁴ ............................................. C12M 1/34
[52] U.S. Cl. .................................... 435/291; 435/285; 324/444
[58] Field of Search ........ 435/291, 285, 287, 299–301; 422/48, 285; 324/444, 446, 439, 450

[56] References Cited

U.S. PATENT DOCUMENTS

| | | |
|---|---|---|
| 3,275,528 | 9/1966 | Ainis ...................... 435/311 X |
| 4,251,631 | 2/1981 | Simon ...................... 435/288 X |
| 4,296,205 | 10/1981 | Verna ...................... 435/285 X |
| 4,686,190 | 8/1987 | Cramer et al. .................. 435/285 X |

OTHER PUBLICATIONS

"Theoretical and Experimental Studies of Transport of Micelle-Solubilized Solutes", by Gregory E. Amidon, William T. Higuchi & Norman F. H. Ho, Accepted for publication Apr. 27, 1981. Journal of Pharmaceutical Sciences, vol. 71, No. 1, Jan. 1982.

*Primary Examiner*—Larry Jones
*Attorney, Agent, or Firm*—Kenyon & Kenyon

[57] ABSTRACT

The system for testing the diffusion behavior of a substance comprises a donor compartment detachably mounted on a holding member of a rotor, rotatably around a vertical axis, said donor compartment being bounded at its bottom by a membrane effective to separate the donor compartment from an acceptor compartment. The membrane comprises a flexible carrier of a bio-compatible, lifeless, light permeable material, on which cells constituting a monocellular layer have been cultivated, for example. By determining the time dependent variation of the quantity of a substance passing through the membrane by diffusion, it is possible to determine the coefficient of diffusion and/or the coefficient of permeability of the membrane and of the cell culture provided thereon. By suitable selection of the cells, conditions may be created that closely resemble those that occur during the absorption of the respective substance through the biophase of a living organism.

29 Claims, 1 Drawing Sheet

MEMBRANE, SYSTEM AND PROCESS FOR TESTING SUBSTANCE DIFFUSION THROUGH THE MEMBRANE AND METHOD FOR MAKING THE MEMBRANE

BACKGROUND OF THE INVENTION

1. Field of the Invention

The present convention concerns a new and improved membrane to be used for testing the diffusion of a substance through said membrane, and in particular for simulating the absorption—by an organism—of an active and/or auxiliary substance contained in a medicine, or of a cosmetic substance, or of a substance to be used in the treatment of plants. The substance may consist of a chemical element or a chemical compound or of a mixture of two or more elements and/or compounds. The invention also concerns a system and a process for testing the diffusion of a substance through said membrane, as well as a method for making the membrane. The invention is to fulfill a need in the fields of physiological and pharmacological research, primarily but not exclusively in conjunction with the absorption of pharmaceuticals by the body of living organisms.

Active substances of orally administered medicines are normally absorbed by the biophase of the respective human or animal by way of the mucous membranes of the stomach and/or the intestines. This absorption takes place at least partially by diffusion. Information regarding the details of the absorption process is of great interest to researchers doing physiological research and/or development and testing of pharmacological products. In order to keep the number of required tests on living organisms low, it is desirable to simulate the absorption in vitro, i.e. outside the body of the living human or animal. Similar problems arise for example if the absorption behavior of the skin covering the body is to be tested with respect to active substances contained in ointments, or with respect to components of cosmetic products. Furthermore, knowledge referring to the absorption behavior of plants is of use, as are treated for example with plant protective chemicals and fertilizers and by necessity absorb substances contained therein, both desirable and undesirable.

2. Description of the Prior Art

In the publication titled "Theoretical and Experimental Studies of Transport of Micelle-Solubilized Solutes" by G. E. Amidon, W. I. Higuchi and N. F. H. Ho as appeared in the Journal of Pharmaceutical Sciences, Vol. 71, 1982, page 77, is disclosed a method performed by means of a system comprising a rotor adapted to be rotated around a vertical axis and comprising a sleeve-shaped wall member. An opening is provided at the lower end of said wall member to make it possible—by means of a clamping sleeve screwed onto the wall member—to fixedly mount two spacer rings, a perforated supporting plate and a lipid-like membrane consisting of dimethylpolysiloxane at said lower end, so that said lipid-like membrane, together with said wall member, will bound a compartment and separate the same from another compartment. Since the membranes used in this known system possess properties greatly deviating from the properties of natural mucous membranes of the stomach and the intestines, it is highly questionable whether the results of the tests performed with said system can be transferred to actual absorption processes as take place in the living organism. If the membranes are lipid-like—particularly when testing substances highly soluble in fat—the danger exists, that these substances will accumulate primarily in the membranes, and the membranes will only inadequately simulate the absorption process through living biomembranes. As a matter of fact, when the membranes are genuine, i.e. living biomembranes, the substances may undergo chemical changes, i.e. they may become metabolized. Furthermore, the fact, that the membrane region in which substance diffusion is possible, is subdivided into relatively small circular subzones by sections provided between the holes of the supporting plate, may cause some problems. Furthermore, it appears to be comparatively troublesome in this known system to first have to temporarily unscrew the clamping sleeve and then fixedly mount the membrane between the supporting plate and one of the spacer rings by screwing the clamping sleeve back in place, and then to separate the membrane again from the wall member after completion of the test.

SUMMARY OF THE INVENTION

Hence form what has been explained heretofore it should be apparent that the art is still in need of a membrane for testing the diffusion of a substance through said membrane, furthermore of a system and process for testing the diffusion of a substance through said membrane and a method for making said membrane, which are not associated with the aforementioned drawbacks and limitations of the state-of-the-art proposals.

It is therefore a primary object of the present invention to provide a novel membrane for testing the diffusion of a substance through said membrane, in particular for simulating the absorption—by an organism—of an active and/or an auxiliary substance contained in a medicine, or of a substance to be used in the treatment of plants, which is not associated with the drawback and limitations of the prior art as heretofore discussed and which effectively and reliably fulfills an existing need in the art. Furthermore, the membrane should have properties closely enough resembling the properties of biomembranes, to make any diffusion test performed with the membrane of the invention adequately simulate the diffusion behavior of the tested substance in a living organism such as a human being, animal or plant.

A further and significant object of the invention relates to a new and improved system for testing substance diffusion through a membrane. This system is to be simple in construction, versatile in its applications and practical in its operation.

Yet another and more specific object of the present invention is to provide a system for testing substance diffusion through a membrane having diffusion properties resembling closely enough those of biomembranes, to have any results obtained in diffusion tests performed with the membrane—for at least one specific substance—yield information relating to the diffusion of said at least one substance through at least one biomembrane.

A further and more specific object of the invention is to provide a system for testing substance diffusion through a membrane and comprising a rotor adapted to be rotated around a vertical axis, the system to enable the membrane provided for diffusion testing to be fastened to the rotor without the risk of any damage of the membrane, to be then brought in position for performing a test and then to be separated from the rotor, this entire process to be performed easily and quickly.

Another significant object of the invention relates to creating a process for testing substance diffusion through a membrane, the process to be adapted to simulate the substance diffusion through the biomembrane of a living organism, and furthermore to be simple, trouble-free and reliable.

Yet another object of the invention relates to a new and improved method for making a membrane such as a membrane having the previously specified features, said method to be simple and sound, and adequate for yielding membranes suited for simulating a variety of diffusion conditions and situations in living organisms.

One of the foregoing objects is attained in accordance with some aspects of the invention, by providing a membrane consisting at least partially of cells derived from and/or made by one or more organisms.

A further foregoing recited object is attained by providing a system equipped with means adapted for detachably holding a membrane and for bounding a first and a second compartment, said two compartments being at least partially separated from each other by said membrane, said membrane to consist at least in part of cells derived from and/or made by at least one living organism.

Another of the foregoing recited objects is attained by providing a system comprising a supporting device and a rotor held by said supporting device rotatably around a vertical axis, furthermore a driving mechanism for rotating the rotor, a wall member detachably connected to one part of the rotor and adapted to detachably hold the membrane, and which wall member—together with the membrane—is adapted to bound said first compartment, said two compartments being so constructed, that during the diffusion test a liquid provided in the second compartment will come in contact with the lower side of at least one region of the membrane, a positioning mechanism being adapted to displace said part of the rotor and said second compartment relative to each other along said axis.

A further of the recited objects is attained by creating a process for testing substance diffusion, that process to comprise the following steps:

(a) The membrane to be used for testing the diffusion is mounted on a front face of a sleeve-shaped wall member, a first compartment bounded by said wall member and said member being thus defined;

(b) Subsequently, the wall member together with the membrane is connected with a rotor held in a supporting device rotatably around a vertical axis, and then the first compartment is brought in contact with a liquid provided in the second compartment and is rotated around said vertical axis;

(c) The quantity of the substance passed from one of the compartments into the other compartment through the membrane by diffusion is determined.

The last object recited above is attained by a method of making a membrane for testing the diffusion through said membrane wherein cells and/or monocellular and/or multicellular organisms are cultivated on a carrier serving as a sheet-like, normally flexible supporting means made of a lifeless material and being at least semipermeable for liquids.

The invention possesses an entire series of advantages.

The membrane may consist for example of a sheet-like flexible carrier made of a lifeless, bio-compatible, preferably hydrophilic material and of cells disposed on the carrier and derived from and/or produced by one or more living organisms, said cells preferably consisting at least in part of live cells. If a membrane is provided for example for simulating the absorption of a substance through the semipermeable mucous membrane of a stomach or of the intestines of a living being, then the membrane as a whole is preferably selected to have—as much as possible—a similar permeability or semipermeability as the mucous membrane to be simulated. If a membrane consists of a carrier and of cells supported by said carrier, then the resistance opposing the diffusion of a substance consists of the carrier resistance and of the cell resistance. Thus, the carrier must be at least semipermeable for liquids, i.e. it must be permeable at least for water and/or another liquid serving as solvent, and permit the passage of molecules of the substance tested as existing in dissolved form, while it may possibly withhold any larger molecules. However, it may be possible to provide a fully permeable carrier, i.e. one that permits the passage of molecules of any size as dissoled or perhaps suspended in a liquid.

The carrier may consist for example of a flexible porous and compact, i.e. apart from the pores continuous film or foil, the pores to form—at least in part—passages penetrating through the carrier, to make the latter become semipermeable or possibly fully permeable. However, the carrier may also consist of a flexible sheet-like textile, such as a woven, knitted or braided tissue, or of a fiber containing composite material, i.e. of felt or fleece. If the carrier consists of a sheet-like piece of textile, it may possess pores and/or openings between adjacent fibers and/or pieces of fibers, and/or perhaps in the fiber material itself, said pores and/or openings being arranged to form—at least in part—passages penetrating through the carrier, and to be for example large enough, to make the carrier not just semipermeable, but fully permeable.

The carrier may be made of a synthetic and/or natural carrier material. Suitable materials for the carrier are for example polyacrylonitrile, polyacrylonitrile-copolymers, cellulose, cellulose acetate, polycarbonate, polycarbonate-copolymers, cotton or a monofilament or multifilament material for seam making as used in surgical operations or for the treatment of wounds, and which may or may not get dissolved inside the body of a living human being or animal. Known synthetic seam making materials that do not dissolve in the body of a living organism may consist for example partially or wholly of polyamide. Seam making materials destined to be used in surgical operations and adapted to be dissolved and absorbabed in the body of a living human being or animal may be of natural origin and consist for example of catgut or may be synthetically made and consist for example partially or wholly of a lactate. Seam making materials that become dissolved and absorbed and are designated as poly-p-dioxanone or coated vicryl (polyglactin 910) are available for instance from Ethicon, a Johnson & Johnson Company. Of the previously mentioned carrier materials at least polyacrylonitrile and copolymers thereof are light permeable (translucent) or even transparent, these being properties of particular advantage.

The carriers may be made of commercially obtainable semipermeable films, as provided for use for hemodialyses. Films of this kind made of polyacrylonitrile or copolymers thereof are obtainable for example from the firm Rhône- Poulenc, Paris, France. Films made of polycarbonate or of its copolymers and used for hemodialyses are made by C. R. Bard Company, Covine, Calif., USA.

The carrier may be provided with various different kinds of cells derived—at least originally—from and/or made by at least one living organism. If for example the absorption of the active substance of a medicine through the walls of the stomach or the intestines is desired to be stimulated, then the proper cells derived from the stomach or the intestines may be cultivated on the carrier and used as a membrane in the test. Such cells of human origin are obtainable from cell banks, while the tests may be performed for example using cells referred to as "Intestine 407" according to international conventions. If, on the other hand, the absorption of the active substance contained in an ointment or a cream, or the absorption of a substance contained in a cosmetic product through the human skin is to be simulated, then the cells to be cultivated on the carrier would be skin cells, or fibrolast cells of the foreskin and/or muscle cells of human origin. The simulation of absorption processes taking place in or on human or animal organisms may be performed evidently by using cultures of animal cells on the carrier. If the absorption—by a plant—of substances used for treating such plants is to be simulated, for example the absorption of components of plant protecting chemicals, fertilizers or other agricultural chemicals, then the cells cultivated on the carrier would be of vegetable origin. Furthermore, mono-and/or multicellular microorganisms, for example seaweed or fungi, may be cultivated on the carrier too.

The system provided for performing the diffusion tests is preferably arranged to comprise a wall member detachably fastened to a rotor of the system by means of a bayonet-joint-like snap closure device, said wall member being of stable shape, specifically ring and/or sleeve shaped, and enclosing an axis, and being arranged to bound—together with the membrane—a donor compartment. The strength of said at least normally flexible membrane and the construction of the wall member are preferably adjusted relative to each other to make that the central region of the membrane extending over the opening of the wall member self-supporting. In other words the membrane should be strong enough to enable a peripheral section of the membrane fastened to the wall member to support said uninterruptedly continuous central membrane region destined to permit the diffusion of a substance without requiring an additional rigid perforated supporting plate.

In order to enable the carrier to be populated with said cells or microorganisms, said wall member is adapted to enable the carrier to be detachably fastened to the wall member, while the latter is separated from the remaining parts of the system. While the carrier is fastened to the wall member separated in this way, the carrier may be inoculated with the proper cells or microorganisms to be cultivated in a sterile incubator.

Since it generally takes considerably longer to cultivate the cells or microorganisms than it takes to perform a test relating to the diffusion behavior and to determine the diffusion coefficient and/or the permeability coefficient of the membrane, the system may be equipped with several wall members of the aforementioned kind. In this way the cells may be cultivated on several carriers at the same time, or in overlapping time intervals, while each carrier is mounted on its own wall member.

Making cultures of cells on a carrier makes it possible to produce membranes comprising each a single layer of cells coalesced with each other, a so-called confluent cell monolayer, or membranes comprising each several layers of cells grown on top of each other, i.e. a living tissue. The cell cultures may be examined microscopically, both during the cultivating process and before carrying out the test of diffusion behavior. This gives the assurance, that the culture will possess the desired structural quality and, for example in the case of a cell monolayer, that it will in fact cover, more or less continuously and preferably completely without interruption, the entire free zone of the carrier, i.e. its entire zone that permits diffusion to take place. If the carriers, for example carriers made of polyacrylonitrile or copolymers thereof, are translucent or transparent, then the microscopic evaluations may be performed by means of through light, i.e. with light permeating the carrier member. This makes the use of a reversing microscope possible for example, this being adapted to facilitate and improve the evaluation of the cell culture. Evidently the cells may be microscopically examined after the test relative to the diffusion behavior. Should microorganisms be cultivated on the carrier, such cultures too may be examined under the microscope in a manner analogous to that mentioned before in conjunction with the cell cultures.

If a carrier fixedly mounted on a wall member has been provided—in its state separated from the rotor, as mentioned before—with a cell culture or with a culture of microorganisms comprising cells, then the wall member—together with the membrane previously fastened to it by means of a fastening member and comprising living cells—may be detachably mounted on the rotor. The mounting process may be carried out so, that the membrane fastened to the wall member will at least essentially not come in contact with any solid part of the system other than said wall member. Correspondingly, the membrane will not be subject—by its being mounted on the rotor—to any mechanical stresses, with the result, that the cells disposed on the membrane carrier will—in spite of their sensitivity to mechanical stresses—not get detached from the carrier or become damaged in any way.

Rather than comprising cultures of cells or microorganisms, the membranes may comprise cells or tissue sections taken as a whole from living animals or humans, or from animal or human corpses. Thus, for example, the membranes may comprise pieces cut out of the walls of the stomach or the intestines, or at least of the mucous membranes thereof, or else of the outer skin of a human or an animal. If these sections of the skin or of another tissue, preferably selected to be alive, possess sufficient mechanical resistance and no holes, they may be mounted in self-supporting fashion on said wall member. Else, they too may be placed on a carrier and mounted to it in some manner.

The membranes according to the invention may be used in particular for testing the absorption of active and/or auxiliary substances in medicines. Substances of this kind are for example salicylic acid, ascorbic acid, urea, sugar, amino acids, peptides, proteins, calcitonine, cyclosporine, interleukine, progesterone and interferone. It is thus possible to test substances having comparatively small molecules, such as amino acids serving as building blocks, and substances of relatively large molecules such as cyclosporine, calcitonine, interleukine, interferone, etc. If the tests are made using membranes having carriers, the carriers may—if necessary—be selected or made—depending on the sizes of the molecules of the substances to be tested—so as to have their throughgoing passages implemented as pores or openings be of smaller or larger cross-sectional dimensions.

During a diffusion test the membrane if effective to separate a donor compartment from an acceptor compartment. The substance to be tested may be introduced into the donor compartment in a form at least partially dissolved in an aqueous solvent and/or possibly in another liquid or pasty solution, and/or dispersed in a liquid, or perhaps bound in liposomes, or in medicine capsules. If a substance contained in an ointment or a cream is to be tested in regard to its absorption, the semisolid ointment or cream may be introduced into the donor compartment. However, the substance is in any case solubilized in a solvent while it diffuses through the membrane.

The substance to be tested is to be preferably marked with a radioactive isotope such as $C^{14}$ or tritium. The acceptor compartment may contain a liquid, preferably aqueous. Should the absorption in the gastro-intestinal tract have to be simulated, for example, then the donor compartment may be provided with a buffer solution having a pH-value corresponding to that of the digestive juices in the stomach or the intestines, respectively. The acceptor liquid provided in the acceptor compartment is continuously circulated through a measuring device comprising a detector adapted to detect radiation, for example a scintillation counter. It is then possible to determine the quantity or the concentration of the substance present in the circulated liquid and passed by diffusion through the membrane, and to calculate in known manner—from the increase in the quantity of the substance—the diffusion coefficient D of the respective substance and/or the permeability coefficient P. The latter is linked to the diffusion coefficient D. This link is represented by the formula $$P = D \cdot K / h$$

in which h is the thickness of the membrane and K the coefficient of distribution. This coefficient K is equal to the ratio of the saturation solubility of the tested substance in the membrane to the saturation solubility of the substance in the solvent.

Assuming a suitable quality or preliminary treatment, the quantities of the substances tested may be calculated from fluorescence or spectrophotometric measurements in place of radioactivity measurements. If the substance to be quantitatively measured is provided in the donor compartment in solution, then it is possible to determine the quantity of the substance passed through the membrane by diffusion, not from the increase in the quantity of substance present in the liquid circulated in the acceptor compartment, but rather from the decrease in the quantity of the substance present in the donor compartment, or from both.

If the liquid provided in the acceptor compartment is at rest relative to the membrane, then a boundary layer in a state of rest will develop near the membrane, resulting in inhibited diffusion. When determining the diffusion coefficient and/or the permeability coefficient, the donor compartment is preferably rotated around a vertical axis, to make the membrane rotate in relation to the acceptor compartment, so that a laminar flow will develop in said acceptor compartment in the region adjacent to the membrane. This laminar flow will cause said boundary layer to become reduced to a comparatively thin layer—more or less in a state of rest relative to the membrane—the thickness of this boundary layer being subject to decrease as the rotational speed increases. It is now possible, for example, to vary the rotational speed of the donor compartment, so as to calculate the permeability for a number of rotational speeds, and—by extrapolating the measurd values—to determine the permeability coefficient corresponding to an infinitely large value of rotational speed. This extrapolated permeability coefficient will then be the permeability coefficient that the membrane would have if the boundary layer were of zero thickness. If the donor compartment comprises a liquid, the latter will more or less rotate together with the donor compartment as the latter is rotated, while—particularly in a case in which the rotational speed is successively increased—an additional flow will become effective to make the boundary layer that develops in the donor compartment and possesses a gradient of substance concentration, become thinner. Apart from the fact that this boundary layer causes less concern than the boundary layer that develops in the acceptor compartment, it is possible to provide, if necessary, one ore more baffle plates stationary in relation to the acceptor compartment and arranged to protrude into the donor compartment, said baffle plate or plates being adapted to exert a braking action on the liquid provided in the donor compartment during the rotation of said liquid, so that the thickness of the boundary layer in the donor compartment may also be reduced—by rotating the latter—to a small value.

If, for testing the diffusion behavior of a certain substance a membrane is used that comprises a carrier and a cell culture cultivated on said carrier, then, in addition to determining the permeability coefficient of the membrane, it is also possible to determine a value for the permeability coefficient for the substance in question in relation to a membrane consisting of the carrier alone. It will then be possible to calculate the difference between the reciprocal values of the two permeability coefficients. The reciprocal value of this difference will then yield the permeability coefficient of the portion of the membrane consisting of the cells alone. If the cells were properly selected, this value will lie comparatively close to the permeability coefficient effective in an organism in vivo, or will be—at least with a very good approximation—proportional to this permeability coefficient.

The system as described in the following in more detail has been used for testing the absorption of salicylic acid, ascorbic acid, urea and the hormone progesterone. A comparison of the calculated permeability coefficients with values published in the literature as having been measured in vivo using the small intestine of rats, has yielded a comparatively good correspondence, particularly for salicylic acid and progesterone.

The close correspondence that may be obtained between measurements carried out in vitro using the system of the invention and the absorption processes that take place in vivo, make it possible to renounce—in certain cases—to a great extent in vivo tests, such as tests on animals. In other cases, however, comparison tests made on living organisms cannot be avoided. Such is the case, for example. if a conversion factor needs to be determined, so as to be able to transfer diffusion coefficients and/or permeability coefficients—as determined by the use of the system of the invention—to in vivo conditions, in man or animal. However, even in these cases, the use of the membrane and system of the invention will make a considerable reduction in the number of required in vivo tests possible.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENTS

Figure 1:
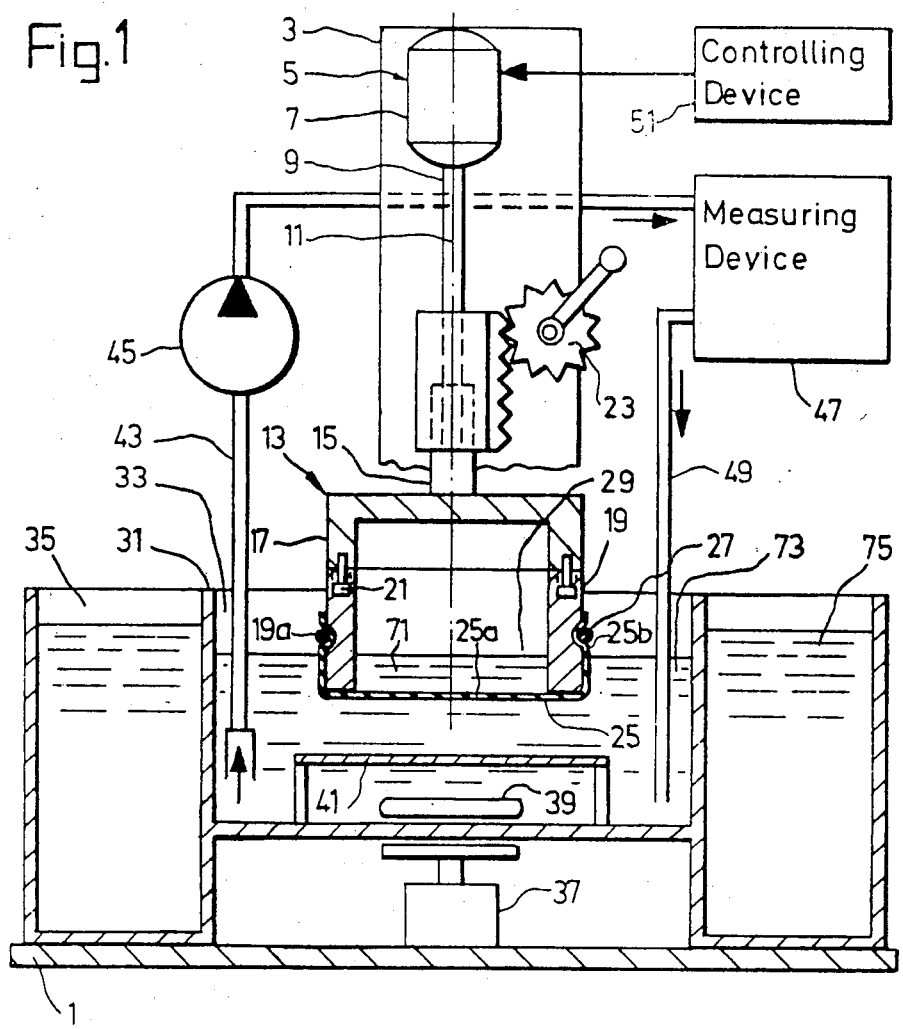
FIG. 1 shows a schematic cross-section of a system for testing diffusion behavior and for determining the coefficient of diffusion and/or permeability.

The system shown in FIG. 1 comprises a base plate 1 arranged to support a supporting device such as a bracket 3, the latter in turn supporting a driving mechanism 5 comprising an electric motor 7 and a shaft 9 disposed rotatably around a vertical axis 11. A rotor 13 comprises a shaft 15, for example hollow, connected to said shaft 9 rotationally rigidly but, for example, adapted to be displaced in axial direction, and a holding member 17 rigidly connected to said shaft 15. The holding member 17 is about cap-shaped and is provided on its top and/or laterally with at least one opening that may be closed for example by a closing means. A sleeve-like hollow cylindrical wall member 19 open at both ends and consisting for example of anodized aluminum is detachably fastened on said holding member 17 by means of the snap closure means 21. The snap closure means 21 is implemented for example as a bayonet-type connection and is arranged to comprise on one of the two components to be connected, for example on the holding member 17, fixedly mounted cams or studs comprising a neck or a shaft and a head radially protruding beyond the shaft and adapted to engage a groove or a slot of the other component. The cylindrical outer surface of the wall member 19 comprises a ring groove 19a disposed below said snap closure means 21. The rotor 13, or at least its holding member 17, is adapted to be displaced, i.e. raised or lowered, along the axis 11 by means of a positioning mechanism 23 adapted for example to be manually actuated, the lowest end position of the rotor 13 shown in FIG. 1 being set by means of at least one stop member. Instead of making the rotor 13 alone displaceable in the axial direction, it could be made vertically displaceable in concert with the entire driving mechanism. A flexible membrane 25 comprises a central section 25a disposed in axial projection inside the inner surface of the wall member 19 and being completely free, i.e. in no contact with any solid component, and possessing the form of a plane circle disposed at the lower ring-shaped end surface of the wall member 19. The membrane 25 also comprises a peripheral section abutting against said end surface of the wall member 19 and surrounding the same. The peripheral section 25b is detachably fastened on the wall member 19 by means of a fastening member 27 consisting of a rubber-like elastic O-ring arranged to press one part of the peripheral section 25 into the ring groove 19a. The wall member 19 is arranged to bound—together with the membrane 25—a first compartment, to be referred to in the following as the donor compartment 29.

A container 31 positioned for example on the base plate 1 and fastened to the same, if required, is arranged to bound a second compartment open on top, the acceptor compartment 33. When in its lower end position shown in FIG. 1, the donor compartment 29 protrudes into the inside of the acceptor compartment 33. The acceptor compartment 33 is surrounded by a ring-shaped chamber 35. A drive device 37 comprising a magnetic clutch is provided below the floor of the acceptor compartment 33 and is arranged to be in magnetic rotational operative connection through said floor with a rod-shaped agitator 39. A disc-shaped cover member 41 is provided between the agitator 39 and the membrane 25.

The acceptor compartment 33 is connected with the inlet of a measuring device 47 by the conduit 43 comprising a suction pump 45, another conduit 49 being arranged to connect the outlet of the measuring device 47 with the acceptor compartment 33. The measuring devic 47 comprises a scintillation counter and a display member, for example digital, and/or a recording device or a printer. The motor 7 is electrically connected to a controlling device 51 adapted to control the motor rotational speed.

Figure 2:
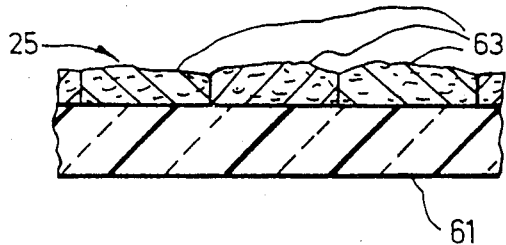
FIG. 2 shows a cross-section through a section of a membrane, at a larger scale.

The membrane separately shown in FIG. 2 comprises a flexible carrier member 61 consisting of a semipermeable film or foil comprising pores that constitute at least partially throughgoing passages. The carrier 61 is made of a lifeless, bio-compatible, hydrophilic, light permeable material such as a polyacrylonitrile-copolymer, and possesses a thickness between 0.01 and 0.03 mm for example. Before the diffusion test the carrier 61 is mounted to the wall member 19 as separated from the rest of the rotor 13, and inoculated with cells 63 on the upper side of its central section 25a, i.e. the region in which diffusion is possible. These cells are then cultivated in an incubator to yield for example a cell monolayer covering the entire central section 25a. The holding member 17 is temporarily raised by means of the positioning mechanism 23 far enough, to enable the donor compartment to be comfortably mounted to the holding member 17. After mounting the donor compartment on the holding member 17 by means of the snap closure means 21, it may be lowered—together with the holding member 17—into its end position shown in FIG. 1. Then, a donor liquid 71 containing the substance to be tested, for example urea marked by radioactive isotope, is introduced into the donor compartment 29 through the opening, or one of the openings of the holding member 17. Furthermore, an acceptor liquid 73 is introduced into the acceptor compartment 33. Subsequent to introducing the donor liquid, the holding member 17 may be brought into a condition, in which it will close off the top of the donor compartment gastight, partially or completely, to prevent vaporization and/or volatilization of the donor liquid. Instead, or in addition thereto, a removable hood could be provided to cover both the acceptor and the donor compartments. The chamber 35 contains a liquid 75.

During the examination of the diffusion behavior the liquid 75 is held at a predetermined temperature, for example at 37° C., by means of a controlling device not shown in the drawing, so that the liquid 73 contained in the acceptor compartment will also be brought to this temperature. The donor compartment, which is immersed with its central membrane section 25a into the liquid 73, is rotated around the axis 11 by the driving mechanism 5. Also the agitator 39 is rotated by the driving device 37, to effect a good mixing of the acceptor liquid 73, while the cover member 41 will prevent the formation of a suction-caused liquid whirl in the region of the membrane. The acceptor liquid 73 is circulated by the pump 45 through the measuring device 47. The quantity or the concentration of the radioactively marked substance present in the acceptor liquid as a result of having been passed by diffusion from the donor compartment into the acceptor compartment is measured by means of the measuring device.

Obviously, numerous modifications and variations of the present invention are possible in the light of the above teachings, It is therefore to be understood that within the scope of the appended claims the invention may be practiced otherwise than is specifically described herein.

Accordingly, what is claimed is:

1. Membrane suitable for use in testing the diffusion of a substance through said membrane, so as to simulate the absorption—by an organism—of an active substance or an auxiliary substance in a medicine, or of a cosmetic substance, or of a substance to be used in the treatment of plants wherein the membrane comprises a sheet-like, liquid permeable or semipermeable, transparent carrier made of lifeless material, and cells supported by the carrier, which are derived from at least one monocellular or multicellular organism.

2. Membrane as claimed in claim 1, wherein at least some of said cells are living cells.

3. Membrane as claimed in claim 1, wherein the carrier is hydrophilic and water permeable.

4. Membrane as claimed in claim 1, wherein said carrier comprises polyacrylonitrile or a copolymer thereof.

5. Membrane as claimed in claim 1, wherein the cells supported by the carrier constitute a cell monolayer and comprise for example intestinal cells, fibroblasts, muscle cells or skin cells.

6. Membrane as claimed in claim 1 wherein the cells supported by the carrier comprise cells derived from a multicellular organism.

7. System for testing the diffusion of a substance through a membrane so as to simulate the absorption—by an organism—of an active or auxiliary substance in a medicine, or of a cosmetic substance, or of a substance to be used in the treatment of plants, the system comprising means adapted for detachably holding a membrane and for bounding the first and a second compartment, said two compartments being at least partially separated from each other by said membrane, said membrane comprising a sheet-like, liquid permeable or semipermeable, transparant carrier made of lifeless material, and cells supported by the carrier which are derived from at least one monocellular or multicellular organism.

8. System as claimed in claim 7, wherein at least some of the cells are live cells.

9. System as claimed in claim 7, comprising a supporting device, furthermore a rotor held by said supporting device rotatably around a vertical axis, a driving mechanism for rotating the rotor, a wall member detachably connected to a part of the rotor and adapted to detachably hold at its lower end the membrane, and which—together with the membrane—is adapted to bound said first compartment, said two compartments being so constructed, that during the diffusion test a liquid provided in the second compartment is brought in contact with the lower side of at least one region of the membrane, a positioning mechanism being adapted to displace said part of the rotor and said second compartment relative to each other along said axis.

10. System as claimed in claim 9, wherein said wall member is connected with said rotor by snap closure means, for example by bayonet-joint-like connecting means.

11. System as claimed in claim 9, further comprising a driving mechanism for driving said rotor with variable rotational speed and a control device connected to the driving device and adapted to control and vary the rotational speed of the rotor.

12. System as claimed in claim 7, wherein the means for detachably holding the membrane and for bounding the two compartments are so constructed, that the region of the membrane adapted to permit the substance to get transferred by diffusion, constitutes a single uninterruptedly continuous section.

13. System as claimed in claim 7, further comprising a radioactivity measuring device for measuring the quantity of said substance diffused from said first compartment through said membrane into said second compartment wherein said substance is marked for radioactivity measurement.

14. System as claimed in claim 13 further comprising a pump for pumping liquid with said substance provided in said second compartment to said measuring device and back to said second compartment.

15. System as claimed in claim 7 further comprising an agitator arranged in said compartment below said membrane and an agitator drive device for rotating said agitator, wherein a cover member is provided between the membrane and the agitator.

16. System is claimed in claim 15, wherein said second compartment is partially limited by a floor and wherein a magnetic clutch is provided that brings said agitator drive device in magnetic operative connection with said agitator through said floor.

17. System for testing the diffusion of a substance through a membrane so as to simulate the absorption—by an organism—of an active substance or an auxiliary substance in a medicine, or of a cosmetic substance, or of a substance to be used in the treatment of plants, the system comprising a supporting device, a rotor held by said supporting device rotatably around a vertical axis, a driving mechanism for rotating the rotor, a wall member detachably connected to a part of the rotor and adapted to detachably hold the membrane, and which—together with the membrane—is adapted to bound said first compartment, said two compartments being so constructed, that during the diffusion test a liquid provided in the second compartment is brought in contact with the lower side of at least one region of the membrane, a positioning mechanism being adapted to displace said part of the rotor and said second compartment relative to each other along said axis, said membrane comprising a sheet-like, liquid permeable or semipermeable, transparent carrier made of lifeless material, and cells supported by the carrier which are derived from at least one monocellular or multicellular organism.

18. System as claimed in claim 17, wherein said wall member and the means for detachably mounting the membrane on said wall member are so constructed, that the region of the membrane adapted to permit the substance to get transferred by diffusion constitutes a single uninterruptedly continuous section, said wall member being connected with the rotor preferably by snap closure means, such as a bayonet-joint-like connecting means.

19. System as claimed in claim 17, further comprising a driving mechanism for driving said rotor with variable rotational speed and a control device connected to the driving device and adapted to control and vary the rotational speed of the rotor.

20. Process for testing the diffusion of a substance through a membrane so as to simulate the absorption—by an organism—of an active substance or an auxiliary substance in a medicine, or of a cosmetic substance, or of a substance to be used in the treatment of plants, the process comprising the steps:
   (a) mounting said membrane comprising a sheet-like, liquid permeable or semipermeable, transparant carrier made of lifeless material on a front face of a sleeve-shaped wall member, a first compartment bounded by said wall member and said membrane being thus defined;
   (b) populating the carrier with living cells derived from at least one monocellular or multicellular organism so that the carrier is a support therefor, the cells on the carrier being microscopially examined at least once by use of light passing through the carrier;
   (c) connecting subsequently the wall member together with the membrane with a rotor held in a supporting device so as to enable rotation around a vertical axis of said wall member, contacting the first compartment with a liquid containing said substance provided in a second compartment, and rotating around said vertical axis; and
   (d) determining the quantity of the substance passed through the membrane from one of the compartments into the other compartment.

21. Process as claimed in claim 20, wherein a living cell monolayer is formed by cultivating said cells on said carrier and wherein at least one microscopial examination of the cells determines whether the monolayer is confluent over the membrane zone through which said substance can diffuse.

22. Process as claimed in claim 20, wherein the zone of said carrier enclosed by sleeve is populated on its upper side by said cells and/or organisms and wherein a reverse microscope is used for examining the microscopically cultivated cells and/or organisms.

23. Process as claimed in claim 20, wherein the microscopic examination of the cultivated cells and/or organisms is made at least once before said quantity of said substance diffused through the membrane is determined.

24. Process as claimed in claim 20, wherein the rotational speed of the wall member and membrane mounted thereto is varied and wherein said quantity of said substance passed through said membrane is determined at different rotational speeds.

25. Process as claimed in claim 20, wherein said substance comprises a dissolved chemical element or compound.

26. Process as claimed in claim 20, wherein said substance comprises a dissolved and/or dispersed active or auxiliary ingredient in a medicine.

27. Process as claimed in claim 20, wherein the substance to be measured is radioactively marked and wherein said quantity of a substance is determined by measuring the radioactivity of a liquid provided in said second compartment after the marked substance has diffused through the membrane.

28. Process a claimed in claim 20 wherein:
   (1) before step (b), determining the quantity of the substance transferred by diffusion through the carrier unpopulated with any cells or organisms by employing said unpopulated carrier in steps (c) and (d);
   (2) calculating a coefficient using the quantities of foregoing step (1) and step (d) of claim 18, that coefficient to characterize the diffusion behavior which the cells or the organisms would show by themselves.

29. Method of making a membrane to be used for the testing the diffusion of a substance through said membrane, so as to simulate the absorption—by an organism—of the active substance or an auxiliary substance in a medicine, or of a cosmetic substance, or of a substance to be used in the treatment of plalnts, wherein cells are cultivated on a carrier made of a lifeless material and which is semipermeable or permeable for liquids.

* * * * *

UNITED STATES PATENT AND TRADEMARK OFFICE
CERTIFICATE OF CORRECTION

PATENT NO. : 4,812,407

DATED : March 14, 1989

INVENTOR(S) : Stephen Buchmann, Hans Leuenberger and Claudia Reinke

It is certified that error appears in the above-identified patent and that said Letters Patent is hereby corrected as shown below:

Column 1, line 41, change "as are" to --as they are--.

Column 1, line 50, before "is disclosed" add --there--.

Column 2, line 22, change "form" to --from--.

Column 4, line 20, change "dissoled" to --dissolved--.

Column 4, line 22, add a comma after "pores."

Column 4, line 51, change "absorbabed" to --absorbed--.

Column 5, line 19, change "fibrolast" to --fibroblast--.

Column 5, line 42, after "make", delete --that--.

Column 8, line 23, change "ore" to --or--.

Column 8, line 64, after "example," delete the period and insert therefor a comma.

Column 11, line 53, change "transparant" to --transparent--.

Column 12, line 35, change "is" to --as--.

Column 13, line 16, change "transparant" to --transparent--.

Column 13, line 24, change "microscopially" to --microscopically--.

Column 13, line 39, change "microscopial" to --microscopic--.

UNITED STATES PATENT AND TRADEMARK OFFICE
CERTIFICATE OF CORRECTION

PATENT NO. : 4,812,407

DATED : March 14, 1989

INVENTOR(S) : Stephen Buchmann, Hans Leuenberger and Claudia Reinke

It is certified that error appears in the above-identified patent and that said Letters Patent is hereby corrected as shown below:

Column 14, line 25, change "a" to --as--.

Column 14, line 37, after "for" delete --the--.

Column 14, line 42, change "plalnts" to --plants--.

Signed and Sealed this

Ninth Day of January, 1990

*Attest:*

JEFFREY M. SAMUELS

*Attesting Officer*     *Acting Commissioner of Patents and Trademarks*